United States Patent
Ide et al.

(10) Patent No.: US 8,080,238 B2
(45) Date of Patent: Dec. 20, 2011

(54) OIL-BASED COSMETIC COMPOSITION

(75) Inventors: Nobuyuki Ide, Yokohama (JP); Sadaki Takata, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 1306 days.

(21) Appl. No.: 11/660,767

(22) PCT Filed: Aug. 22, 2005

(86) PCT No.: PCT/JP2005/015588
§ 371 (c)(1),
(2), (4) Date: Feb. 22, 2007

(87) PCT Pub. No.: WO2006/022395
PCT Pub. Date: Mar. 2, 2006

(65) Prior Publication Data
US 2007/0292377 A1    Dec. 20, 2007

(30) Foreign Application Priority Data

Aug. 24, 2004 (JP) .................. 2004-244345
Apr. 1, 2005 (JP) .................. 2005-105626
Aug. 5, 2005 (JP) .................. 2005-228835

(51) Int. Cl.
*A61Q 1/10* (2006.01)
(52) U.S. Cl. ................... 424/70.7; 424/401
(58) Field of Classification Search .......... None
See application file for complete search history.

(56) References Cited

U.S. PATENT DOCUMENTS 6,482,400 B1 * 11/2002 Collin .................... 424/70.6

FOREIGN PATENT DOCUMENTS

| JP | 58-180414 | * | 10/1983 |
| JP | 2639417 | | 5/1997 |
| JP | 2001-19613 | | 1/2001 |
| JP | 2001019613 | * | 1/2001 |
| JP | 2002-193747 | | 7/2002 |
| JP | 2002-265328 | | 9/2002 |
| JP | 200363927 | | 3/2003 |
| JP | 2003-521489 | | 7/2003 |
| JP | 2005-89309 | | 4/2005 |

* cited by examiner

*Primary Examiner* — Jyothsna Venkat
(74) *Attorney, Agent, or Firm* — Foley & Lardner LLP

(57) ABSTRACT

An oil-based cosmetic composition having high temperature stability, giving a coating film after evaporation of a solvent having a high gloss, and excellent in forming of a coloring material when the coloring matter, particularly a hair cosmetic composition such as mascara, etc., containing (a) a dextrin fatty acid ester, (b) a sucrose fatty acid ester having an average substitution degree of the ester of 3 to 8, and (c) an optional oil component which is solid at 30° C. in an amount of 5 mass % or less and, if desired, (d) a fluid oil which is liquid at 30° C. (i.e., not evaporating at an ordinary temperature) in an amount of 1 to 50 mass %, (e) a coloring material in an amount of 0.01 to 30 mass %, (f) a coating agent in an amount of 1 to 40 mass %, and (g) a volatile oil in an amount of 30 to 80 mass %.

5 Claims, No Drawings

US 8,080,238 B2

OIL-BASED COSMETIC COMPOSITION

TECHNICAL FIELD

The present invention relates to an oil-based cosmetic composition, more specifically an oil-based hair cosmetic composition such as mascara etc. More particularly, it relates to an oil-based cosmetic composition excellent in high temperature stability, giving a coating film having a high gloss after evaporation of a solvent (e.g., volatile oil etc.), and excellent in color formation of the coloring material when the coloring material is formulated.

BACKGROUND ART

Hair cosmetic compositions represented by mascara, etc. are required to make the lashes look thicker and longer, give the lashes a feeling of volume, and give other effects and also give cosmetic composition staying power effects over time (e.g., water resistance, skin oil resistance), curl effects (e.g., fast drying capability and effects of causing lashes to curl upward), curl holding effects (e.g., effect of retaining curl over time), and other functional effects.

In recent years, demands have been increasing for oil-based cosmetic compositions which can not only give hair a volume effect and curl effect, but can also give the hair sufficient gloss to make the hair itself appear alive and beautiful and further can bring out to the maximum the color forming characteristic of the coloring material or pearl agent, lame agent, and gloss substance to be formulated.

However, if containing/a large amount of solid oil components such as wax so as to improve the volume effects and curl effects (e.g., see Japanese Patent Publication (A) No. 2003-521489), the composition per se becomes opaque, the coating film after evaporation of the solvent becomes a clouded matte quality, and the gloss of the coated hair per se are lost.

Further, if solid oil components such as wax are formulated, the color formation of the coloring material or the color forming characteristic of glossy substances such as a pearl agent or lame agent becomes weak, and therefore, these materials have to be incorporated thereto in large amounts.

If a dextrin fatty acid ester etc. used as an oil-based gelling agent in the past is used, a preparation having a high transparency of the coating film can be obtained (e.g., see Japanese Patent No. 2639417), but if included in a large amount, the oil-based gel per se becomes strong and uniform application of coating becomes difficult, and therefore, the inclusion in a large amount was not possible.

Similarly, a sucrose fatty acid ester has been used for the purpose of the curl effect or volume effect in hair cosmetic compositions such as mascara since the past. An eyelash cosmetic composition containing a sucrose fatty acid ester having an average substitution degree of the ester of 3 to 8 has also been studied (e.g., see Japanese Patent Publication (A) No. 58-180414).

However, dried coating films after coating give a matte quality in each case. The color forming capability of the coloring material was not sufficiently satisfactory, either.

Further, in each study, the study was conducted on a base of a water-base or water-in-oil type or oil-in-water type of emulsion system. Even when implements such as an eyelash curler are used to physically curl the eyelashes, at the end, the base caused the eyelashes to be moistened with water, and therefore, a sufficient effect could not be obtained in the point of retention of the curl effect along with the time.

On the other hand, even in a lipstick or gloss, an oil-based cosmetic composition is being sought which can give the sufficient gloss and further can bring out to the maximum the color forming characteristic of the coloring material or pearl agent, lame agent, and gloss substance to be formulated thereto.

Further, excellent stability as a cosmetic composition is also sought.

Note that, as an oil-based cosmetic composition excellent in water resistance, cosmetic composition staying power, stability, usability, etc., a non-water based (or oil-based) cosmetic composition containing isoparaffin in an amount of 40 to 80 mass %, a new oil-based gelling agent having sucrose or dextrin, as a basic structure, in an amount of 5 to 20 mass %, and waxes in an amount of 10 to 30 mass % is proposed (see Japanese Patent Publication (A) No. 2003-63927), but such a cosmetic composition includes a large amount of waxes, and therefore, at the end, the dried coating film after coating gave a matte quality in each case and the color forming capability of the coloring material was also not sufficiently satisfactory.

DISCLOSURE OF THE INVENTION

The present invention was completed in consideration of the above situation and has an object of the provision of an oil-based cosmetic composition which is excellent in high temperature stability, gives a coating film after evaporation of a solvent (e.g., volatile oil etc.) having a high gloss, and is excellent in color forming capability of the coloring material when a coloring material is used.

The present invention has a further object to provide an oil-based hair cosmetic composition which, when used as a hair cosmetic composition, not only has the above effects, but is also excellent in feeling of volume, curl effects, and curl holding effects.

That is, the present invention relates to an oil-based cosmetic composition comprising a cosmetic composition base, in which (a) a dextrin fatty acid ester, (b) a sucrose fatty acid ester having an average substitution degree of ester of 3 to 8, and (c) an optional oil, component, which is solid at 30° C., are contained in an amount of 5 mass % (or wt %, the same hereinbelow), based upon the total amount of the oil-based cosmetic composition.

The present invention further relates to the above oil-based cosmetic composition comprising a cosmetic composition base and 5 to 40 mass % of the component (a) and 5 to 50 mass % of the component (b), based upon the total amount of the oil-based cosmetic composition.

The present invention relates to the above oil-based cosmetic composition further comprising (d) an oil component, which is liquid at 30° C. (i.e., liquid oil not evaporating at an ordinary temperature) in an amount of 1 to 50 mass %, based upon the total amount of the oil-based cosmetic composition.

The present invention relates to the above oil-based cosmetic composition further comprising (e) a coloring material in an amount of 0.01 to 30 mass %, based upon the total amount of the oil-based cosmetic composition.

The present invention relates to the above oil-based cosmetic composition further comprising (f) a coating agent in an amount of 1 to 40 mass %, based upon the total amount of the oil-based cosmetic composition.

The present invention relates to the above oil-based cosmetic composition further comprising (g) a volatile oil in an amount of 30 to 80 mass %, based upon a cosmetic composition base.

The present invention further relates to the above oil-based cosmetic composition wherein a hardness at 30° C. (Card Tensionmeter: 8 mmϕ/200 g load value) is in the range of 10 to 150.

The present invention further relates to the above oil-based cosmetic composition which is a hair cosmetic composition (here, a mode in which the hair cosmetic composition is an eyelash cosmetic composition is preferable).

In accordance with the present invention, there is provided an oil-based cosmetic composition excellent in stability (in particular, stability at a high temperature) and gloss imparting property and excellent in color forming capability of coloring matter when a coloring material is formulated. Further, when used as a hair cosmetic composition, there is provided an oil-based cosmetic composition not only having the effect, but also giving an excellent feeling of volume, curl effects, curl holding effects, and separation effects.

BEST MODE FOR CARRYING OUT THE INVENTION

The inventors engaged in intensive research to solve the above problem and, as a result, found that, by combining a dextrin fatty acid ester, a sucrose fatty acid ester having an average substitution degree of the ester of 3 to 8, and an oil which is solid at 30° C. in an amount of 5 mass % or less (including 0 mass %), it is possible to provide an oil-based cosmetic composition excellent in high temperature stability, giving a coating film after evaporation of a solvent having a high gloss, and excellent in color forming capability of the coloring matter when further containing coloring material and, when used as a hair cosmetic composition, it is possible to obtain an oil-based hair cosmetic composition not only having the above effects, but also excellent in feeling of volume, curl effects, and curl holding effects, whereby the present invention has been completed.

The oil-based cosmetic composition and oil-based hair cosmetic composition of the present invention will now be described in detail.

Note that, the "hair" in the present invention is a generic name including head hair and body hair. The oil-based hair cosmetic composition of the present invention may be also used for head hair, for eyelashes, and for eyebrows and is most preferably used as eyelash oil-based cosmetic composition such as a mascara.

The dextrin fatty acid ester (a) usable in the present invention is an ester of dextrin or reduced dextrin with a higher fatty acid.

The average sugar polymerization degree of the above dextrin or reduced dextrin is preferably 3 to 100.

Further, as the higher fatty acid, a $C_8$ to $C_{16}$ saturated fatty acid is preferably used.

Specifically, octanoic acid, lauric acid, myristic acid, palmitic acid, etc. may be mentioned. These higher fatty acids may be used alone or more.

In the present invention, as the component (a), a dextrin fatty acid ester obtained by esterification by reacting one or more types of dextrin or reduced dextrin having an average polymerization degree of glucose of 3 to 100 and one or more types of $C_8$ to $C_{16}$ saturated fatty acids using a tertiary amine as a catalyst in the presence of water or one or more types of alcohol in an amount of 3.0 to 50.0 mass %, based upon the total amount of dextrin so as to obtain a substitution degree of the saturated fatty acid of 1.2 to 2.4, based upon the glucose unit of the dextrin or a dextrin fatty acid ester obtained by washing the dextrin fatty acid ester with water and alcohol are preferably used.

The component (a) is available on the market as "Rheopearl® KL", "Rheopearl® MKL", "Rheopearl® TT" (all of above made by Chiba Seifun), etc. These may be suitably used.

The formulating amount of the component (a) is suitably adjusted depending upon the composition, but is preferably 5 to 40 mass %, more preferably 10 to 35 mass %. If the formulating amount is less than 5 mass %, the gloss effects, volume effects, and curl effects given to the dried coating film are not sufficient, and therefore, it is difficult to obtain the effects of cosmetic compositions such as mascara. Further, there is little effects as a gelling agent, the oil-based gel is difficult to stably maintain, and satisfactory results in quality are not obtained. On the other hand, if the formulating amount of the component (a) is more than 40 mass %, the dried coating film is given an extremely high gloss (or glossiness), but if the oil-based gel is strong in coagulating force, the dried coating film exhibits cracks, the coating film lacks uniformity, and therefore, the gloss (or glossiness) is decreased, uniform adhesion to the hair becomes difficult, and the desired cosmetic composition effect becomes difficult to obtain. Further, the oil-based gel itself becomes extremely strong, and therefore, uniform coating on the hair as a cosmetic composition becomes difficult. This is not preferable from this point as well.

In the present invention, as the component (b), a sucrose fatty acid ester having an average substitution degree of the ester of 3 to 8 is used. The average substitution degree of 5 to 8 is more preferable. As the component (b), for example, those shown in, for example, Japanese Patent Publication (B2) No 53-6220 such as a sucrose fatty acid ester having an average substitution degree of a $C_6$ to $C_{24}$ saturated or unsaturated fatty acid of 3 or more, a sucrose fatty acid ester having an average substitution degree of a $C_6$ to $C_{24}$ saturated or unsaturated fatty acid and an average substitution degree of a $C_2$ to $C_4$ lower fatty acid totaling 3 or more, etc. may be mentioned.

As preferred specific examples of such an oil-soluble high substitution degree sucrose fatty acid ester, sucrose tetrastearyl tetraacetate, sucrose pentastearate, sucrose tetraisostearate, sucrose tetrapalmityl tetrabutylate, etc. may be exemplified. Here, the "substitution degree" of the ester means the average value of the number of bonds of the ester-bonded fatty acid per molecule of component sucrose of a sucrose fatty acid ester.

In the present invention, the component (b) having an ester ratio of the mono-, di-, or tri-mer or more of 5:95 to 0:100 gives a uniform oil-based gel composition and gives a coating film having a high gloss. Since the oil-based gel per se thus obtained has transparency, when a coloring material is formulated, the color forming capability of the coloring material becomes excellent. Therefore, this is preferably used.

The formulating amount of the component (b) is suitably adjusted according to the composition, but is preferably 5 to 50 mass %, more preferably 10 to 45 mass %. If the formulating amount is less than 5 mass %, this is not enough to give gloss effects, volume effects, or curl effects, to the dried coating film, and therefore it is difficult to obtain these effects in cosmetic compositions such as a mascara. Further, there is also little effects as a gelling agent, it is difficult to stably hold an oil-based gel, and a satisfactory quality cannot be obtained. On the other hand, if the formulating amount is more than 40 mass %, an extremely high gloss (glossiness) is given to the dried coating film, but when the coagulating force of the oil-based gel is strong, after drying, the coating film shows cracks and the coating film lacks uniformity so the gloss (or glossiness) is decreased and uniform application to the hair becomes difficult, and therefore, it becomes difficult to obtain the desired cosmetic composition effect. Further, the oil-based gel per se becomes extremely strong, and therefore, uniform coating on the hair as a cosmetic composition becomes difficult. Further, the oil-based gel per se is extremely sticky. When coated on the hair, it sticks causing the hairs to form bundles. It remains sticky even after time elapses after coating. Therefore, the phenomenon of secondary adhesion where the coloring material etc. included sticks to the skin occurs. The cosmetic composition staying power is remarkably poor. This is therefore not preferable.

In the present invention, further, from the viewpoint of the temperature stability or volume effects, curl effects, etc. of the hair cosmetic composition, the oil component (c), which is solid at 30° C., is included in an amount of 5 mass % or less, based upon the entire amount of the cosmetic composition. If the formulating amount of the component (c) is more than 5 mass %, the gloss of the coating film after evaporation of the solvent tends to decrease. Further, even if the coloring material is formulated, the color forming capability tends to decrease. If within a range where temperature stability of quality can be secured, it is preferable not to include the component (c).

As specific examples of the component (c), paraffin, microcrystalline wax, polyethylene wax, candelilla wax, carnauba wax, beeswax, Japan wax, jojoba ester, synthetic wax, etc. may be mentioned. Note that, the component (a) and component (b) are not included in the component (c).

In the present invention, by formulating the component (a) to the component (b) and the component (c) in a specific amount or less in combination, the outstanding effect is exhibited of obtaining an oil-based cosmetic composition excellent in high temperature stability, giving a coating film after evaporation of a solvent having a high gloss, and having an excellent color forming capability of the coloring matter. These effects are remarkable effects which are not able to be predicted from the prior art.

For example, in a formulation of only the component (a) ingredient among the component (a) and the component (b), while a base with gloss can be obtained, there is the problem that it is inferior in high temperature stability (e.g., when held at 50° C. or less for 1 week, the liquid oil component bleeding out, the coloring material etc. settling and separating, etc.) If the formulating amount of the component (a) is increased in such a system so as to try to maintain a high temperature stability, while the glossiness is somewhat increased, the coagulating capability of the gel per se is increased, and therefore, the coating film after evaporation of a solvent shows cracks, the gel per se becomes harder, and uniform coating becomes difficult, and therefore, there is a limit to the formulating amount and a gloss of a satisfactory extent cannot be obtained.

On the other hand, by formulating just the component (b), since the component (b) tends to become weaker in gelling capability compared with the component (a), a satisfactory oil-based gel cannot be obtained, but a liquid is formed and the coloring material becomes precipitating (or dispersability of coloring material deteriorates), and therefore an oil-based cosmetic composition containing coloring material cannot be obtained.

By formulating the component (a) ingredient and the component (b) and the component (c) in a specific amount or less in combination, first, gloss is given and excellent high temperature stability is obtained. By formulating coloring material, etc., a base excellent in color forming capability of the coloring material becomes possible.

Note that, in the present invention, if formulating a sucrose fatty acid ester having an average substitution degree of ester of less than 3, it becomes difficult to sufficiently obtain the effects due to the combination of the components (a) to (b) and a specific amount or less of the component (c), and therefore, it is preferable not to include a sucrose fatty acid ester having an average substitution degree of the ester of less than 3 in the cosmetic composition.

In the present invention, in addition to the components (a) to (b) and the specific amount or less of the component (c), by formulating the oil component (d) which is liquid at 30° C. (or a liquid oil not evaporating at an ordinary temperature), it is possible to improve the gloss of the coating film after drying and to improve the coating film strength. The component (d) is not particularly limited so long as it is one generally used for a makeup cosmetic composition. For example, hydrocarbon oils such as heavy isoparaffin, squalane, liquid paraffin; esters such as cetyl-2-ethylhexanoate, 2-ethylhexyl palmitate, 2-octyldodecyl myristate, neopentyl glycol-2-ethylhexanoate, isopropyl myristate, myristyl myristate; lipids such as olive oil, avocado oil, jojoba oil, sunflower oil, safflower oil, tsubaki oil, macadamia nut oil, mink oil, liquid lanolin, lanolin acetate, castor oil; silicone-based oil ingredients such as dimethyl polysiloxane, methylphenyl polysiloxane, high polymerization degree gum-like dimethyl polysiloxane, polyether-modified silicone, amino-modified silicone; fluorine-based oil ingredients such as fluorine-modified dimethyl polysiloxane, fluorine-modified methylphenyl polysiloxane, perfluoropolyether, perfluorocarbon and etc. may be mentioned.

The formulating amount of the component (d) is suitably adjusted depending upon the form of the composition, but is preferably 1 to 50 mass %, more preferably 5 to 45 mass %. If less than 1 mass %, the dried coating film shows cracks etc., the finish does not become uniform, and the dried coating film sometimes flakes off along with the elapse of time. On the other hand, if more than 50 mass % is blended, a dried coating film cannot be obtained in the finishing stage. The coating film remains sticky forever. This is not satisfactory for use as a cosmetic composition.

In the present invention, further, by formulating the coloring material (e), compared with a conventional oil-based hair cosmetic composition, the colors of the coloring matter, pearl agent, lame agent, etc. can be reflected in the finish as they are. A high gloss is given in the finish, and therefore, a makeup effect having a sharp color formation can be given.

The component (e) usable in the present invention is not particularly limited so long as it is one generally used for a makeup cosmetic composition, but a hydrophobic one is preferably used. For example, inorganic pigments such as talc, mica, kaolin, calcium carbonate, zinc white, titanium dioxide, red iron oxide, yellow iron oxide, black iron oxide, ultramarine blue, carbon black, lower titanium oxide, cobalt violet, chromium oxide, chromium hydroxide, cobalt titanate, bismuth oxychloride, mica titanium-based pearl pigment; organic pigments such as Red No. 201, Red No. 202, Red No. 204, Red No. 205, Red No. 220, Red No. 226, Red No. 228, Red No. 405, Orange No. 203, Yellow No. 205, Yellow No. 4, Yellow No. 5, Blue No. 1, Blue No. 404, Green No. 3 and other zirconium, barium or aluminum lakes; natural colors such as chlorophyll, β-carotin; resin powders such as nylon, cellulose, polyethylene; dyes, etc. may be mentioned. The component (e) may be used alone or more.

The formulating amount of the component (e) is suitably adjusted depending upon the form of the composition, but is preferably 0.01 to 30 mass %, more preferably 0.5 to 25 mass %. If formulating more than 30 mass %, the coating film becomes matte-like in quality and the desired gloss is detracted therefrom.

Note that, in the oil-based cosmetic composition of the present invention, even if the component (e) is not included, use as a transparent oil-based base is possible. For example, it is possible to impart gloss to the hair, without being governed by the difference in color of the hair due to ethnicity. That is, it is possible to give a lively gloss to the hair, without detracting from the color of the hair of the individual.

Further, this transparent oil-based base is not limited to a hair cosmetic composition. Application to another makeup product (e.g., a stick-type transparent lipstick etc.) becomes possible.

In the present invention, by further formulating the coating agent (f), it is possible to obtain a high resistance to sweat, tears, skin oil, etc., hold that effect for a long period of time from right after the application of coating to after the elapse of considerable time, and suppress secondary adhesion (transfer) to other locations (hair or skin). In particular it is possible to impart an effect of increasing the curl retention of the eyelashes in a hair cosmetic-like mascara. The component (f) is not particularly limited so long as it is a resin usually formulated into a cosmetic composition as an agent for forming a coating film. Specifically, latexes of a polyvinyl alcohol, polyvinyl pyrrolidone, polyvinyl acetate, alkylpolyacrylate; cellulose derivatives such as dextrin, alkyl cellulose or nitrocellulose; silicone resins such as trimethyl siloxysilicic acid; silicone-based resins such as trimethyl siloxysilyl propyl carbamide acid, fluorine-modified silicone resin, acryl silicone copolymer resin; a fluorine resin; aromatic hydrocarbon resin; polymer emulsion resin; terpene-based resin; polybutene; polyisoprene; alkyd resin; polyvinyl pyrrolidone-modified polymer; rosin-modified resin; polyurethane; etc. may be used. As a fluorine resin, a perfluoroalkyl-group including acryl resin, perfluoroalkyl-group including methacryl resin or other hydrocarbon-based resin having a perfluoroalkyl group, at a pendant form, in the main chain of the system; a polyvinylidene fluoride or other such resin where the main chain itself is a fluorocarbon; a resin having both a hydrocarbon part and fluorocarbon part at the main chain obtained by radical copolymerization of a fluoroethylene and hydrocarbon-based vinyl ether, etc. may be mentioned, but the present invention is not limited to these Examples.

Among these, in particular, a silicone-based resin is preferable. Among these, trimethyl siloxysilicic acid [commercial product of "KF7312J®" or "X-21-5250®" (both made by Shin-etsu Silicone), etc.) or tri(trimethylsiloxy)silyl carbamidic acid (made by Shin-etsu Silicone) may be used, but the present invention is not limited to these.

The formulating amount of the component (f) is suitably adjusted, depending upon the composition, but is preferably 1 to 40 mass %, more preferably 5 to 35 mass %. If the formulating amount is less than 1 mass %, sufficient curl effects and curl holding effects cannot be obtained and, further, cosmetic composition staying powers such as the effects of the water resistance, sweat resistance, skin oil resistance, are poor. On the other hand, if the formulating amount is more than 40 mass %, the oil-based gel tends to become softer in hardness and uniform coating on the hair becomes difficult. Further, the drying takes too much time, the individual hairs easily bundle together (i.e., no separation effect), and stickiness becomes remarkable, so this is not preferable.

In the present invention, by further formulating the component (g) volatile oil (i.e., oil having volatility at an ordinary temperature), it is possible to impart a fast drying capability of the finish, suppress secondary adhesion (transfer) to other locations (e.g., hair or skin), retain the curl effects and curl effects due to the same, etc.

The component (g) usable in the present invention is not particularly limited so long as it is one generally used for a makeup cosmetic composition. For example, lower alcohols such as ethanol; cyclic silicone oils such as decamethyl cyclopentasiloxane, dodecamethyl cyclohexasiloxane; or hydrocarbons such as light isoparaffin, etc. may be mentioned.

The formulating amount of the component (g) is suitably adjusted, depending upon the form of the composition, but is preferably 30 to 80 mass %, more preferably 40 to 70 mass %. If the formulating amount is less than 30 mass %, it is not sufficient for dissolving the other components for forming the preparation, other than the volatile oil and a uniform cosmetic composition able to withstand use cannot be obtained. On the other hand, if more than 80 mass % is formulated, the preparation does not become hard and remains a liquid, and therefore cannot be uniformly coated on the hair, etc. Further, it is difficult to maintain the stability of the system.

The oil-based cosmetic composition of the present invention preferably has a hardness in the range of 10 to 150 at 30° C. (Card Tensionmeter; 8 mm+/200 g load). The "hardness" referred to here is the hardness of the oil-based cosmetic composition before drying. It is the value measured under conditions of 30° C. using a measuring device Model M-301AR Card Tensionmeter (made by Iio Electric) and a load of 200 g on an 8 mmφ probe. If the hardness at 30° C. is less than 10, uniform coating on each and every hair becomes difficult. Further, the drying takes too much time, the individual hairs easily bundle together, stickiness becomes remarkable, and a beautiful finish as a cosmetic composition cannot be obtained, and therefore, this is not preferable. On the other hand, if the hardness at 30° C. is more than 150, the oil-based gel per se becomes strong and uniform coating on the skin, hair, etc. becomes difficult, and therefore, this is not preferred.

In the oil-based cosmetic composition of the present invention, by further formulating a metal soap, the gel strength can be effectively held, and therefore, it becomes possible to adjust the usability according to the object, while securing temperature stability at a high temperature. As the metal soap, a higher fatty acid salt of a nonalkali metal (calcium, zinc, magnesium, etc.) may be used. Specifically, for example, aluminum stearate, aluminum palmitate, calcium stearate, zinc stearate, zinc myristate, magnesium myristate, etc. may be mentioned, but the invention is not limited to these. Among these, from the viewpoint of not allowing the dried coating film to decrease in the gloss, aluminum stearate, aluminum palmitate, and magnesium myristate are preferably used.

In the oil-based cosmetic composition of the present invention, when formulating a metal soap, the formulating amount of the metal soap, while suitably adjusted depending upon the composition, is preferably 0.1 to 5 mass %, more preferably 0.5 to 3 mass %. If the formulating amount is less than 0.1 mass %, the effect as a gelling agent is difficult to sufficiently obtain. On the other hand, if the amount blended is more than 5 mass %, fibrillation of the gel occurs, and the gel per se becomes too strong in some cases.

The oil-based cosmetic composition of the present invention is not particularly limited in the application therefore, but, since the coating film after evaporation of a solvent has a high gloss and the color forming capability of the coloring material is good, the cosmetic composition is preferably used as a mascara, eyebrow pencil, eye pencil or other such hair cosmetic composition or an eyeliner, lipstick, lipgloss, lipcream, etc.

The form of the oil-based cosmetic composition of the present invention is not particularly limited, but preferably forms a solid, paste, or powder or a liquid in a range having a viscosity of an extent enabling a pigment to be stably dispersed.

The oil-based cosmetic composition of the present invention may further contain, according to the object, ingredients able to be normally formulated into a makeup cosmetic composition or hair care cosmetic composition to a range of quantity and quality not detracting from the effects of the present invention. As such ingredients, for example, fibers, alcohols, polyhydric alcohols, medicines, surfactants, polymers, clay minerals, preservatives, fragrances, anti-oxidants, UV absorbents, humectants, lipids, hydrocarbon oil, and other oil-based ingredients etc. may be mentioned, but the present invention is not limited thereto.

EXAMPLES

The present invention will now be explained in further detail by Examples, but the present invention is not limited to these Examples. Unless the formulating amounts are specially indicated, they are shown by the mass % of the ingredients based upon the system formulated.

Samples A to D and Samples E to H (Study of Color Forming Capability, Gloss and High Temperature Stability)

As the means for obtaining curl effects and volume effects in a hair cosmetic composition (mascara), in the past the general practice had been to formulate a wax, but as shown in Tables I to II, samples comprised of the system of the present invention including the component (a) and the coloring material plus waxes (more than 5 mass %) (=Samples B, C, F, G), samples including the component (b) (=Samples D, H), and samples not including the waxes or the component (b) (=control and Samples A, E) were prepared.

Further, Samples B, C, F, and G including waxes (more than 5 mass %), Samples D, H including the component (b), and Samples A, E (controls) not including either waxes or the component (b) were examined as to two points: (i) how much of a color difference (ΔE) there is, in other words, how much the color of the coloring material included is formed, without inhibition (excellence of color forming ability), and (ii) how much the gloss can be maintained (color difference and gloss), using red coloring material (Table I) and black coloring material (Table II). The high temperature stability was also evaluated. The method of evaluation was shown below. The results are shown in Tables I and II.

Measurement of Color Difference

The control and the samples were measured using a spectroscopy system (made by Macbeth) to find the color difference from the control (ΔE).

Measurement of Glossiness

An inside liquid sample was coated on color matching paper (OPACITY CHARTS FORM 5C (194×260 mm), made by the Leneta Company) to a uniform thickness (doctor blade 0.35 mm thick). This was allowed to stand to dry for one day and night at an ordinary temperature to prepare a detected sample. A glossiness meter (NIPPON DENSHOKU GLOSS METER VG2000) was used. The average value of the measurement values (n=5) was defined as the glossiness.

Evaluation of High Temperature Stability

Each sample was packed into a transparent glass cream container, was allowed to stand in a 50° C. incubator for 4 weeks, then was visually examined.

Evaluation Criteria

Very good: No bleedout of oil or precipitation of coloring material, separation of system, etc. seen.

Good: Some bleedout of oil or precipitation of coloring material, separation of system, etc. seen, but not considered particular problem in actual use.

Fair: Small bleedout of oil or precipitation of coloring material, separation of system, etc. seen, but within allowable range in actual use.

Poor: Bleedout of oil or precipitation of coloring material, separation of system, etc. seen and use becomes difficult.

TABLE I

|  | Sample A (control) | Sample B | Sample C | Sample D |
|---|---|---|---|---|
| Formulation (% by weight) | | | | |
| Light isoparaffin | Bal. | Bal. | Bal. | Bal. |
| Polyethyleneglycol dioleate | 2 | 2 | 2 | 2 |
| Diglyceryl diisostearate | 2 | 2 | 2 | 2 |
| Dimethyldistearyl ammonium hectorite | 0.5 | 0.5 | 0.5 | 0.5 |
| Phenyl trimethicon | 5 | 5 | 5 | 5 |
| Dextrin (palmitate/octanoate)[*1] | 25 | 25 | 25 | 25 |
| Microcrystalline wax | — | 10 | — | — |
| Polyethylene wax | — | — | 10 | — |
| Mixed fatty acid sucrose[*2] | — | — | — | 10 |
| Hydrophobically treated coloring material (red) | 5 | 5 | 5 | 5 |
| Evaluation | | | | |
| Color difference from control (ΔE) | — | 0.496 | 1.291 | 0.471 |
| Gloss (average value of glossiness n = 5) | 70.9 | 9.4 | 14.4 | 74.8 |
| High temperature stability | Poor | Good | Very good | Good |

TABLE II

|  | Sample E (control) | Sample F | Sample G | Sample H |
|---|---|---|---|---|
| Formulation (% by weight) | | | | |
| Light isoparaffin | Bal. | Bal. | Bal. | Bal. |
| Polyethyleneglycol dioleate | 2 | 2 | 2 | 2 |
| Diglyceryl diisostearate | 2 | 2 | 2 | 2 |
| Dimethyldistearyl ammonium hectorite | 0.5 | 0.5 | 0.5 | 0.5 |
| Phenyl trimethicon | 5 | 5 | 5 | 5 |
| Dextrin (palmitate/octanoate)[*1] | 25 | 25 | 25 | 25 |
| Microcrystalline wax | — | 10 | — | — |
| Polyethylene wax | — | — | 10 | — |
| Mixed fatty acid sucrose[*2] | — | — | — | 10 |
| Hydrophobically treated coloring material (black) | 5 | 5 | 5 | 5 |
| Evaluation | | | | |
| Color difference from control (ΔE) | — | 0.121 | 0.42 | 0.127 |
| Gloss (average value of glossiness n = 5) | 49.5 | 8.3 | 11.8 | 56.4 |
| High temperature stability | Poor | Good | Very good | Good |

Note that in Tables I and II, for the "dextrin (palmitate/octanoate)[*1]", "Rheopearl® TT" (made by Chiba Seifun) was used.

For the "mixed fatty acid sucrose[*2]", "Cosmelike® MX-10" (made by Dai-ichi Kogyo Seiyaku) was used (ester substitution degree 5 to 6; component fatty acid: oleic acid about 40%, palmitic acid about 30%, stearic acid about 30%; monoester:di-triester or more=about 0:about 100).

As is clear from the results shown in Table I, by formulating waxes into a system including the component (a) and coloring material (red) (see Samples B, C), it was possible to suppress the remarkably declining gloss, while by formulating the component (b) instead of a wax (see Sample D), it was possible to suppress the action of reduction of the gloss and also possible to improve the gloss over the control (Sample A). Further, it was possible to realize a smaller color difference (ΔE) and sharp red over the control (Sample A).

As is clear from the results shown in Table II, by formulating waxes into a system including the component (a) and coloring material (black) (see Samples F, G), it was possible to suppress the remarkably declining gloss, while by formulating the component (b) instead of a wax (see Sample H), it was possible to suppress the action of the decline in gloss and also possible to improve the gloss over the control (Sample E). Further, it was possible to obtain a smaller color difference (ΔE) with respect to the control (Sample E) and reproduce a sharper black color.

Examples 1 to 6 and Comparative Examples 1 to 3

Samples (mascara) of the compositions shown in the following Tables III to IV were prepared by the usual methods and used to evaluate the curl effects, curl retention effects, volume effects, gloss, color forming ability, separation effects, high temperature stability, and hardness by the following evaluation methods. The results are shown in Table III to IV.

Curl Effect, Curl Retention Effect, Volume Effect, Gloss After Coating, Color Forming Ability, and Separation Effect An expert panel of 20 coated each sample (mascara) on their eyelashes 10 times and evaluated the conditions by the naked eye by the following criteria. Note that the curl retention effect, gloss after coating, and color forming capability were evaluated at the elapse of 3 hours from coating.

Evaluation of Curl Effect
Very good: Out of 20 panelists, 16 panelists or more responding there is curl effect
Good: Out of 20 panelists, 10 to 15 panelists responding there is curl effect
Fair: Out of 20 panelists, 5 to 9 panelists or more responding there is curl effect
Poor: Out of 20 panelists, 4 or less responding there is curl effect Evaluation of Curl Retention Effect (Evaluation 3 Hours After Coating)
Very good: Out of 20 panelists, 16 panelists or more responding there is curl retention effect
Good: Out of 20 panelists, 10 to 15 panelists responding there is curl retention effect
Fair: Out of 20 panelists, 5 to 9 panelists or more responding there is curl retention effect
Poor: Out of 20 panelists, 4 or less responding there is curl retention effect Evaluation of Volume Effect
Very good: Out of 20 panelists, 16 panelists or more responding there is volume effect
Good: Out of 20 panelists, 10 to 15 panelists responding there is volume effect
Fair: Out of 20 panelists, 5 to 9 panelists or more responding there is volume effect
Poor: Out of 20 panelists, 4 or less responding there is volume effect Evaluation of Gloss of Eyelashes (Evaluation 3 Hours After Coating)
Very good: Out of 20 panelists, 16 panelists or more responding there is gloss
Good: Out of 20 panelists, 10 to 15 panelists responding there is gloss
Fair: Out of 20 panelists, 5 to 9 panelists or more responding there is gloss
Poor: Out of 20 panelists, 4 or less responding there is gloss Evaluation of Color Forming Ability of Eyelashes (Evaluation 3 Hours After Coating)
Very good: Out of 20 panelists, 16 panelists or more responding color forming ability is excellent
Good: Out of 20 panelists, 10 to 15 panelists responding color forming ability is excellent
Fair: Out of 20 panelists, 5 to 9 panelists or more responding color forming ability is excellent
Poor: Out of 20 panelists, 4 or less responding color forming ability is excellent Separation Effect
Very good: Out of 20 panelists, 16 panelists or more responding there is separation effect
Good: Out of 20 panelists, 10 to 15 panelists responding there is separation effect
Fair: Out of 20 panelists, 5 to 9 panelists or more responding there is separation effect
Poor: Out of 20 panelists, 4 or less responding there is separation effect High Temperature Stability
Each sample was held at 50° C. for 4 weeks, then was visually evaluated for appearance.

Evaluation Criteria
Very good: No bleedout of oil or precipitation of coloring material, separation of system, etc. seen.
Good: Some bleedout of oil or precipitation of coloring material, separation of system, etc. seen, but not considered particular problem in actual use.
Fair: Small bleedout of oil or precipitation of coloring material, separation of system, etc. seen, but considered within allowable range in actual use.
Poor: Bleedout of oil or precipitation of coloring material, separation of system, etc. seen and use becomes difficult.

Hardness
Each sample was measured for hardness under conditions of 30° C. using a measuring device Model M-301AR Card Tensionmeter (made by Iio Electric) and a load of 200 g on an 8 mmϕ probe.

TABLE III

| | Ex. 1 | Ex. 2 | Ex. 3 | Ex. 4 | Ex. 5 |
|---|---|---|---|---|---|
| Formulation ((% by weight) | | | | | |
| Light isoparaffin | Bal. | Bal. | Bal. | Bal. | Bal. |
| Dimethyl polysiloxane | 3 | 3 | 3 | 3 | 3 |
| Decamethylcyclopentasiloxane | 5 | 5 | 5 | 5 | 5 |
| Octyl palmitate | 1 | 1 | 1 | 1 | 1 |
| Isostearic acid | 1 | 1 | 1 | 1 | 1 |
| Microcrystalline wax | 1 | — | — | — | — |
| Carnauba wax | 2 | — | — | — | — |
| Beeswax | 2 | — | — | — | — |
| Dextrin(palmitate/octanoate)(*1) | 15 | 15 | 15 | 30 | 30 |
| Mixed fatty acid sucrose(*2) | 30 | 30 | — | 15 | — |
| Sucrose acetostearate(*3) | — | — | 30 | — | 15 |
| Trimethyl siloxysilicic acid | 10 | 10 | 10 | 10 | 10 |
| Hydrophobically treated coloring material (black) | 3 | 3 | 3 | 3 | 3 |
| DL-α-tocoferol acetate | 0.1 | 0.1 | 0.1 | 0.1 | 0.1 |
| Preservative | q.s. | q.s. | q.s. | q.s. | q.s. |
| Fragrance | q.s. | q.s. | q.s. | q.s. | q.s. |
| Evaluation | | | | | |
| Curl effect | Very good | Very good | Very good | Very good | Very good |
| Curl retention effect | Very good | Good | Very good | Good | Very good |
| Volume effect | Very good | Very good | Very good | Very good | Very good |
| Gloss | Good | Very good | Very good | Very good | Very good |
| Color forming capability | Good | Very good | Very good | Very good | Very good |

TABLE III-continued

|  | Ex. 1 | Ex. 2 | Ex. 3 | Ex. 4 | Ex. 5 |
|---|---|---|---|---|---|
| Separate effect | Good | Good | Very good | Good | Very good |
| High temperature stability | Very good | Fair | Good | Good | Very good |
| Hardness | 50 | 10 | 25 | 40 | 80 |

TABLE IV

|  | Ex. 6 | Comp. Ex. 1 | Comp. Ex. 2 | Comp. Ex. 3 |
|---|---|---|---|---|
| Formulation (% by weight) |  |  |  |  |
| Light isoparaffin | Bal. | Bal. | Bal. | Bal. |
| Dimethyl polysiloxane | 3 | 3 | 3 | 3 |
| Decamethyl cyclopentasiloxane | 5 | 5 | 5 | 5 |
| Octyl palmitate | 1 | 1 | 1 | 1 |
| Isostearic acid | 1 | 1 | 1 | 1 |
| Microcrystalline wax | — | 10 | 1 | 5 |
| Carnauba wax | — | 2 | 2 | 2 |
| Beeswax | — | 2 | 2 | 2 |
| Dextrin (palmitate/octanoate)(*1) | 15 | 15 | 30 | — |
| Mixed fatty acid sucrose(*2) | — | — | — | — |
| Sucrose acetostearate(*3) | 45 | — | — | 30 |
| Trimethyl siloxysilicic acid | 5 | 10 | 10 | 10 |
| Hydrophobically treated coloring material (black) | 3 | 3 | 3 | 3 |
| DL-α-tocoferol acetate | 0.1 | 0.1 | 0.1 | 0.1 |
| Preservative | q.s. | q.s. | q.s. | q.s. |
| Fragrance | q.s. | q.s. | q.s. | q.s. |
| Evaluation |  |  |  |  |
| Curl effect | Very good | Very good | Good | Very good |
| Curl retention effect | Very good | Very good | Good | Good |
| Volume effect | Very good | Good | Good | Very good |
| Gloss | Very good | Poor | Fair | Fair |
| Color forming capability | Very good | Poor | Good | Fair |
| Separate effect | Good | Good | Fair | Good |
| High temperature stability | Very good | Poor | Poor | Poor |
| Hardness | 45 | 70 | 50 | 35 |

Note that in Tables III to IV, for the "dextrin (palmitate/octanoate)(*1)", "Rheopearl® TT" (made by Chiba Seifun) was used.

For the "mixed fatty acid sucrose(*2)", "Cosmelike® MX-10" (made by Dai-ichi Kogyo Seiyaku) was used (ester substitution degree 5 to 6; component fatty acid:oleic acid about 40%, palmitic acid about 30%, stearic acid about 30%; monoester:di-triester or more=about 0:about 100).

For the "sucrose acetostearate(*3)", "Cosmelike® SA-10" (made by Dai-ichi Kogyo Seiyaku) was used (ester substitution degree 8; component fatty acid:stearic acid about 70%).

Examples 7 to 10 and Comparative Examples 4 to 6

Samples of the compositions shown in the following Tables V to VI (mascara) were prepared by the usual method and used for evaluation according to the above evaluation methods. The results are shown in Tables V to VI. In Comparative Example 5 the coloring material was precipitated in liquid state before solidification to paste formation.

TABLE V

|  | Comp. Ex. 4 | Comp. Ex. 5 | Ex. 7 | Ex. 8 |
|---|---|---|---|---|
| Formulation (% by weight) |  |  |  |  |
| Light isoparaffin | Bal. | Bal. | Bal. | Bal. |
| Dextrin palmitate(*4) | 5 | — | 5 | 5 |
| Dextrin(palmitate/octanoate)(*1) | 15 | — | 15 | 15 |
| Microcrystalline wax | — | — | — | 1 |
| Sucrose acetostearate(*3) | — | 10 | 10 | 10 |
| Sucrose tetraisostearate(*5) | — | 1 | 1 | 1 |
| Isostearic acid | 2.5 | 2.5 | 2.5 | 2.5 |
| Glyceryl tri-2-ethylhexanoate | 1 | 1 | 1 | 1 |
| Decamethyl cyclopentasiloxane | 5 | 5 | 5 | 5 |
| Trimethyl siloxysilicic acid | 5 | 5 | 5 | 5 |
| Hydrophobically treated coloring material (black) | 5 | 5 | 5 | 5 |
| DL-α-tocoferol acetate | 0.01 | 0.01 | 0.01 | 0.01 |
| Preservative | q.s. | q.s. | q.s. | q.s. |
| Fragrance | q.s. | q.s. | q.s. | q.s. |
| Evaluation |  |  |  |  |
| Curl effect | Fair | — | Very good | Very good |
| Curl retention effect | Fair | — | Very good | Very good |
| Volume effect | Fair | — | Good | Good |
| Gloss | Good | — | Very good | Good |
| Color forming capability | Very good | — | Very good | Very good |
| Separate effect | Very good | — | Very good | Very good |
| High temperature stability | Poor | — | Very good | Very good |
| Hardness | 8 | — | 28 | 36 |

TABLE VI

|  | Ex. 9 | Ex. 10 | Comp. Ex. 6 |
|---|---|---|---|
| Formulation (% by weight) |  |  |  |
| Light isoparaffin | Bal. | Bal. | Bal. |
| Dextrin palmitate(*4) | 5 | 5 | 5 |
| Dextrin (palmitate/octanoate)(*1) | 15 | 15 | 15 |
| Microcrystalline wax | 3 | 5 | 10 |
| Sucrose acetostearate(*3) | 10 | 10 | 10 |
| Sucrose tetraisostearate(*5) | 1 | 1 | 1 |
| Isostearic acid | 2.5 | 2.5 | 2.5 |
| Glyceryl tri-2-ethyl hexanoate | 1 | 1 | 1 |
| Decamethyl cyclopentasiloxane | 5 | 5 | 5 |
| Trimethyl siloxysilicic acid | 5 | 5 | 5 |
| Hydrophobically treated coloring matter (black) | 5 | 5 | 5 |
| DL-α-tocoferol acetate | 0.01 | 0.01 | 0.01 |
| Preservative | q.s. | q.s. | q.s. |
| Fragrance | q.s. | q.s. | q.s. |
| Evaluation |  |  |  |
| Curl effect | Very good | Very good | Very good |
| Curl retention effect | Good | Good | Good |
| Volume effect | Very good | Very good | Very good |
| Gloss | Good | Fair | Poor |
| Color forming capability | Good | Good | Fair |
| Separate effect | Good | Good | Fair |
| High temperature stability | Very good | Very good | Very good |
| Hardness | 40 | 52 | 78 |

Note that in Table V to VI, for the "dextrin (palmitate/octanoate)(*1)", "Rheopearl® TT" (made by Chiba Seifun) was used, while for the "dextrin palmitate(*4)", "Rheopearl® KL" (made by Chiba Seifun) was used.

For the "sucrose acetostearate(*3)", "Cosmelike® SA-10" (made by Dai-ichi Kogyo Seiyaku) was used (ester substitution degree 8; component fatty acid:stearic acid about 70%).

For the "sucrose tetraisostearate(*5)", "Crodesta® 4-IS" (made by Croda Japan) was used (ester substitution degree about 4; monoester: di-triester or more=about 0 to 0.5: about 1: about 98.5 to 99 (tetraester 50% or more)).

Example 11

Lipstick

| Formulation ingredients | Mass % |
| --- | --- |
| Candelilla wax | 2 |
| Carnauba wax | 3 |
| Sucrose acetostearate (ester average substitution degree about 8) | 20 |
| Dextrin palmitate ("Rheopearl ® KL"; made by Chiba Seifun) | 10 |
| Disostearyl maleate | 5 |
| Glyceryl diisostearate | 1 |
| Trimethylol propane trioctanoate | 0.5 |
| Glyceryl tri-2-ethylhexanoate | Bal. |
| Dibasic calcium phosphate | 1 |
| Silicone coated pigment (titanium oxide) | q.s. |
| Silicone coated pigment (bengara) | q.s. |
| Barium sulfate | 2 |
| Carmine Coated Titanated Mica | 2 |
| Dye | q.s. |
| Heavy liquid isoparaffin | 10 |

Example 12

Lipgloss

| Formulation ingredients | Mass % |
| --- | --- |
| Liquid paraffin | Bal. |
| Sucrose mixed fatty acid ester ("Cosmelike ® MX-10"; made by Dai-ichi Kogyo Seiyaku) | 40 |
| Glyceryl tri-2-ethylhexanoate | 10 |
| Silicone coated pigment (iron oxide) | 0.1 |
| Silicone coated pigment (titanium oxide) | 0.1 |
| Silicone coated pigment (bengara) | 0.1 |
| Barium sulfate | 0.1 |
| Bengara coated mica | q.s. |
| δ-tocoferol | 0.1 |
| Color | q.s. |
| Dextrin myristate ("Rheopearl ® MKL"; made by Chiba Seifun) | 15 |
| Heavy liquid isoparaffin | 2 |

Example 13

Mascara

| Formulation ingredients | Mass % |
| --- | --- |
| Light isoparaffin | Bal. |
| Dimethyl polysiloxane | 3 |
| Decamethyl cyclopentasiloxane | 5 |
| Octyl palmitate | 1 |
| Isostearic acid | 1 |
| Microcrystalline wax | 1 |
| Carnauba wax | 2 |
| Beeswax | 2 |
| Dextrin (palmitate/octanoate) | 15 |
| Sucrose mixed fatty acid ester ("Cosmelike ® MX-10"; made by Dai-ichi Kogyo Seiyaku) | 20 |
| Sucrose tetraisostearate ("Crodesta ® 4-IS"; made by Croda Japan) | 10 |
| Trimethyl siloxysilicic acid | 5 |
| Aluminum stearate | 1 |
| Silicone coated pigment (iron oxide) | 0.5 |
| Silicone coated pigment (titanium oxide) | 0.3 |
| Silicone coated pigment (bengara) | 0.2 |
| Barium sulfate | 0.1 |
| Bengara-coated mica | q.s. |
| δ-tocoferol | 0.1 |

The invention claimed is:

1. An oil-based cosmetic composition comprising a cosmetic composition base, 10-35 mass % of (a) a dextrin fatty acid ester selected from dextrin palmitate and dextrin palmitate/octanoate, 10-45 mass % of (b) a sucrose fatty acid ester having an average substitution degree of ester of 3 to 8 selected from sucrose acetostearate and sucrose tetraisostearate and (c) an oil component which is solid at 30° C. in an amount of 5 mass % or less, based upon the total amount of the oil-based cosmetic composition, and selected from microcrystalline wax, polyethylene wax, carnauba wax and beeswax, wherein the cosmetic composition is an eyelash cosmetic composition.

2. An oil-based cosmetic composition as claimed in claim 1, further comprising (d) an oil component which is liquid at 30° C. (a fluid oil not evaporating at an ordinary temperature) in an amount of 1 to 50 mass %, based upon the total amount of the oil-based cosmetic composition.

3. An oil-based cosmetic composition as claimed in claim 1, further comprising (e) a coloring material in an amount of 0.01 to 30 mass %, based upon the total amount of the oil-based cosmetic composition.

4. An oil-based cosmetic composition as claimed in claim 1, further comprising (f) a coating agent in an amount of 1 to 40 mass % based upon the total amount of the oil-based cosmetic composition.

5. An oil-based cosmetic composition as claimed in claim 1, further comprising (g) a volatile oil in an amount of 30 to 80 mass % with respect to the total amount of the oil-based cosmetic composition.

* * * * *